(12) United States Patent
Hagert

(10) Patent No.: US 7,935,115 B2
(45) Date of Patent: May 3, 2011

(54) SYSTEM FOR FIXATION OF FRACTURES COMPRISING AN ELASTIC CHASSIS

(75) Inventor: Carl-Göran Hagert, Bjärred (SE)

(73) Assignee: General Orthopedics Int. AB, Linkoping (SE)

( * ) Notice: Subject to any disclaimer, the term of this patent is extended or adjusted under 35 U.S.C. 154(b) by 64 days.

(21) Appl. No.: 10/825,128

(22) Filed: Apr. 16, 2004

(65) Prior Publication Data

US 2004/0210228 A1    Oct. 21, 2004

(30) Foreign Application Priority Data

Oct. 29, 2001 (SE) ...................................... 0103575

(51) Int. Cl.
*A61F 5/04* (2006.01)
(52) U.S. Cl. .......................................... 606/54; 606/280
(58) Field of Classification Search ............. 606/54–59, 606/61, 69–72, 257, 280, 282–285, 289–291
See application file for complete search history.

(56) References Cited

U.S. PATENT DOCUMENTS

| | | | | |
|---|---|---|---|---|
| 1,789,060 A | * | 1/1931 | Weisenbach | ................... 606/54 |
| 3,877,424 A | * | 4/1975 | Murray | ........................... 606/54 |
| 4,893,618 A | * | 1/1990 | Herzberg | ........................ 606/54 |
| 5,458,599 A | * | 10/1995 | Adobbati | ........................ 606/56 |
| 5,462,547 A | | 10/1995 | Weigum | |
| 5,603,713 A | | 2/1997 | Aust et al. | |
| 5,954,722 A | | 9/1999 | Bono | |
| 6,206,881 B1 | | 3/2001 | Frigg et al. | |
| 6,206,882 B1 | * | 3/2001 | Cohen | ............................. 606/69 |
| 6,228,085 B1 | * | 5/2001 | Theken et al. | .................. 606/61 |
| 6,290,703 B1 | | 9/2001 | Ganem | |
| 6,530,925 B2 | * | 3/2003 | Boudard et al. | ................. 606/54 |

FOREIGN PATENT DOCUMENTS

| | | |
|---|---|---|
| JP | 50141882 | 11/1975 |
| JP | 11512004 | 10/1999 |
| SE | 509703 C2 | 3/1999 |
| WO | WO 90/07304 A1 | 7/1990 |

* cited by examiner

*Primary Examiner* — Thomas C Barrett
*Assistant Examiner* — Michael J Araj
(74) *Attorney, Agent, or Firm* — Tarolli, Sundheim, Covell & Tummino LLP

(57) ABSTRACT

A system for fixation of fractures is disclosed. The system comprises a chassis and one or more fixation elements in the form of screws and/or pins. Each fixation element is received in the chassis in such a way that it is locked by friction regarding movement in axial, rotational and angular directions. The friction is preferably given by the material of the chassis having an elasticity giving locking effect by friction on the fixation elements.

12 Claims, 2 Drawing Sheets

SYSTEM FOR FIXATION OF FRACTURES COMPRISING AN ELASTIC CHASSIS

TECHNICAL FIELD

The present invention concerns a system for fixation of fractures. The system is mainly intended for external fixation, but it may also be used for internal fixation. It may be used on any fractured bone of both humans and animals.

PRIOR ART

Fractured bones are normally fixated by means of different internal fixations, external fixature or a plaster cast. All the different fixation methods have both drawbacks and advantages.

Existing fixation systems often use metal plates having predrilled clearance holes in which screws are to be received. The screws are pulled down towards the metal plate, whereby the underlying bone structure will have to adapt to the hard rigid metal plate. This may risk both deformation and dislocation of the bone structure. As the known plates bear against the bone, the blood circulation is impaired. It is known to have plates with gaps to reduce these problems.

The Invention

It is one object of the present invention to have a fixation system avoiding the problems with a rigid plate pressed against a bone structure.

A further object is to have a fixation system, which is easy to adapt to the location and form of the actual fracture. It is also an object to have a fixation system that may be used with relative ease and that has a relatively low price.

The above objects are met by a system for fixation of fractures comprising a chassis and one or more fixation means. The fixation means are screws and/or pins. Each fixation element is to be received in the chassis in such a way that it is locked by friction regarding movement in axial, rotational and angular directions.

Preferably the chassis is made of a material locking the fixation means by friction.

The present invention will not give rise to any stress on the bone structure caused by the force of the fixation. It could be said that by the invention cortex is extended in order to enable for fixation means to be inserted. The chassis is placed at any distance from the bone structure. By the present invention it is possible to "transfer" internal fixations to more simplistic external fixations.

The chassis is preferably made of a polymer and may be formed in accordance with the anatomy at the fractured area. Form and thickness etc. are much easier to vary for polymer materials compared to details made of a metal. The system of the present invention may be manufactured at a much lower cost than metal products.

The system of the present invention is much more comfortable for a patient to carry compared to e.g. a plaster cast or any of the existing external fixatures. The system may be used without locking a joint during healing if needed and without exerting any force on the joint. Thus, the risk of having complications with a stiff joint after healing of the fracture is avoided.

The present fixation system may be used for any bone independent of size and form. The system has many advantages such as less need for rehabilitation, better healing and more comfortable wear for the patient. The fixation system will normally be in place for 5 to 6 weeks.

Further objets and advantages will be obvious for a person skilled in the art when reading the detailed description below of a preferred embodiment.

BRIEF DESCRIPTION OF THE DRAWINGS

The invention will be explained further below by way of an example and with reference to the enclosed drawings. In the drawings.

DETAILED DESCRIPTION OF PREFERRED EMBODIMENTS

Figure 1:
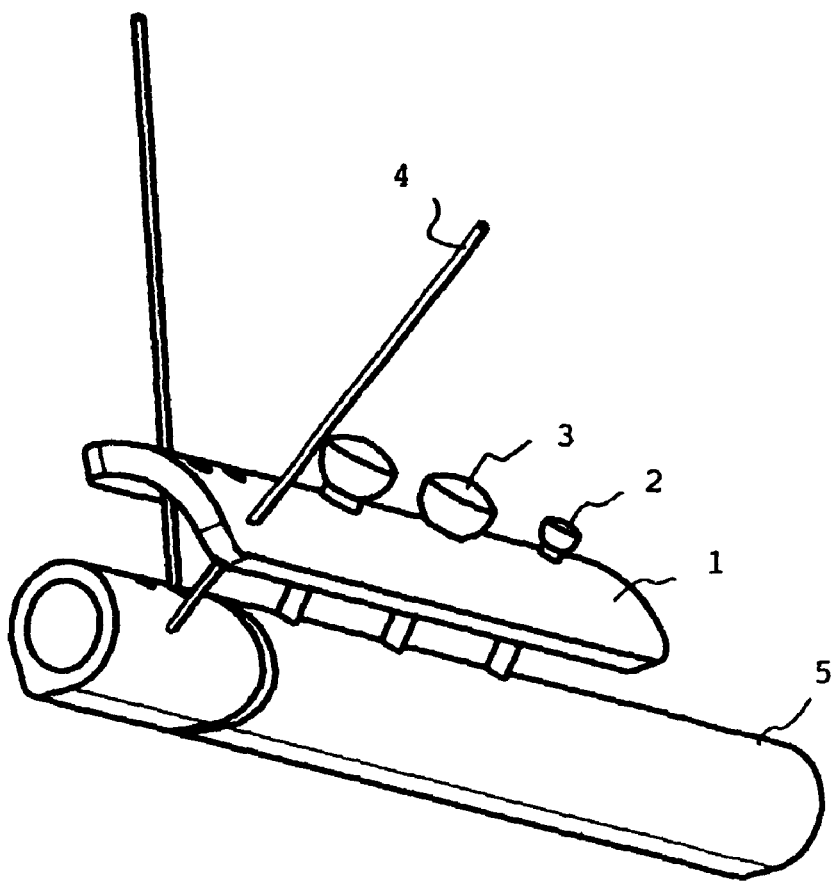
FIG. 1 is a perspective view of a system for fixation according to a first embodiment of the present invention.

The system comprises a chassis 1, one or more screws 2, 3 and one or more pins 4. In some embodiments the chassis 1 is received in a bracing 6.

The chassis 1 is made of a material, which locks the inserted screws 2, 3 and/or pins 4 by means of friction. The screws 2, 3 and pins 4 are all locked in view of rotation, axial movements and angular movements. One material that may be used for the chassis 1 is UHMWPE (ultra high molecular weight polyethylene). UHMWPE is generally approved for medical use both externally and internally and is also transparent for X-rays. Other materials having the same characteristics may also be used, e.g. different kinds of polymers.

The form of the chassis 1 may be adapted to the size of the bone and the form of the anatomy at the location of the fracture(s) to be fixated. Thus, there will be a wide range of different designs for the chassis 1 regarding both size and form.

The screws 2, 3 used will be of standard type. Screws 2, 3 of different size may be used for the same chassis 1. Also the used pins 4 are of a standard type. For small fractured parts and bones pins 4 are preferably used, as a screw 2, 3 would cause further fragmentation. As an example pins 4 having a diameter of 2 mm has been inserted into channels having a diameter of 1 mm in the chassis 1. The channels will guide the insertion of the pins 4 in the desired direction and due to their smaller diameter will be locked.

When the fracture has been satisfyingly reduced the chassis 1 is placed over the fractured area. Then holes are predrilled through the chassis 1, the skin and the bone structure 5. The chassis 1 may be furnished with a number of holes at manufacture, which may be used if appropriate. In some embodiments the chassis 1 will be given no holes at manufacture. A screw 2, 3 or a pin 4 is then screwed into each desired predrilled hole. The chassis 1 is held at any chosen distance from the bone during and after fixation. The screws 2, 3 have the same pitch, which means that the chassis 1 will not move during fixation. Thus, there is always a gap between the body and the chassis 1. The chassis 1 will not be in direct contact with the underlying bone structure 5 or skin.

The screws 2, 3 are screwed in synchronously, i.e. the screw 2, 3 will move equidistantly in the bone structure 5 and the chassis 1. Thus, no forces will be generated in the axial direction of the screw 2, 3 and a force neutral fixation of the chassis 1 and bone structure 5 will be accomplished. Pins 4 and further screws 2, 3 are applied in the same way at optional locations according to the preference of the surgeon. As the chassis 1 has been fixed to the bone structure 5 on both sides of the fractured area a "bridge span" has been formed between the bone fragments. This "bridge span" will now guarantee that the bone fragments are fixated and are in a rigid condition relative each other. The formed "bridge span" may be described as a parallel shift of cortex of the bone structure 5 to the outside, whereby it is possible to transfer internal fixations to external fixations when the system of the present invention is used. This transfer is very much sought after as the number of surgical operations may be reduced and often eliminated. The chassis 1, screws 2, 3 and pins 4 are removed when the fracture has healed in the desired way.

The surgeon is free to place the screws 2, 3 and pins 4 optimally, as he himself decides exactly where the holes, and thus the screws 2, 3 and pins 4, are to be placed at the actual operation. Previously known fixation devices or plates normally have openings the placing of which is given at manufacture. Thus, the surgeon has to compromise regarding the placing of the previously known fixation elements. With the present invention the surgeon may decide "on the fly" where the optimal locations are for the screws 2, 3 and pins 4.

The material of the chassis 1 gives a frictional force on the screws 2, 3 or pins 4 which is big enough to guarantee that they are not screwed out or will come lose in any other way. This is a problem with previous plates made of a metal and having "clearance holes".

The material of the chassis 1 is chosen to give sufficient bending rigidity to allow the fracture to heal. This bending rigidity eliminates the risk of braking, which is a well known complication for plates made of steel etc.

Figure 3:
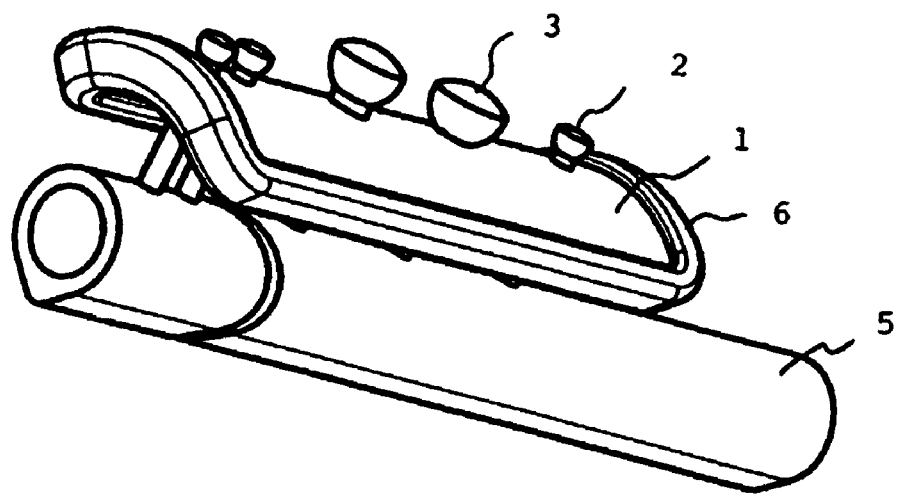
FIG. 3 is a perspective view of a second embodiment of the present invention.
Figure 4:
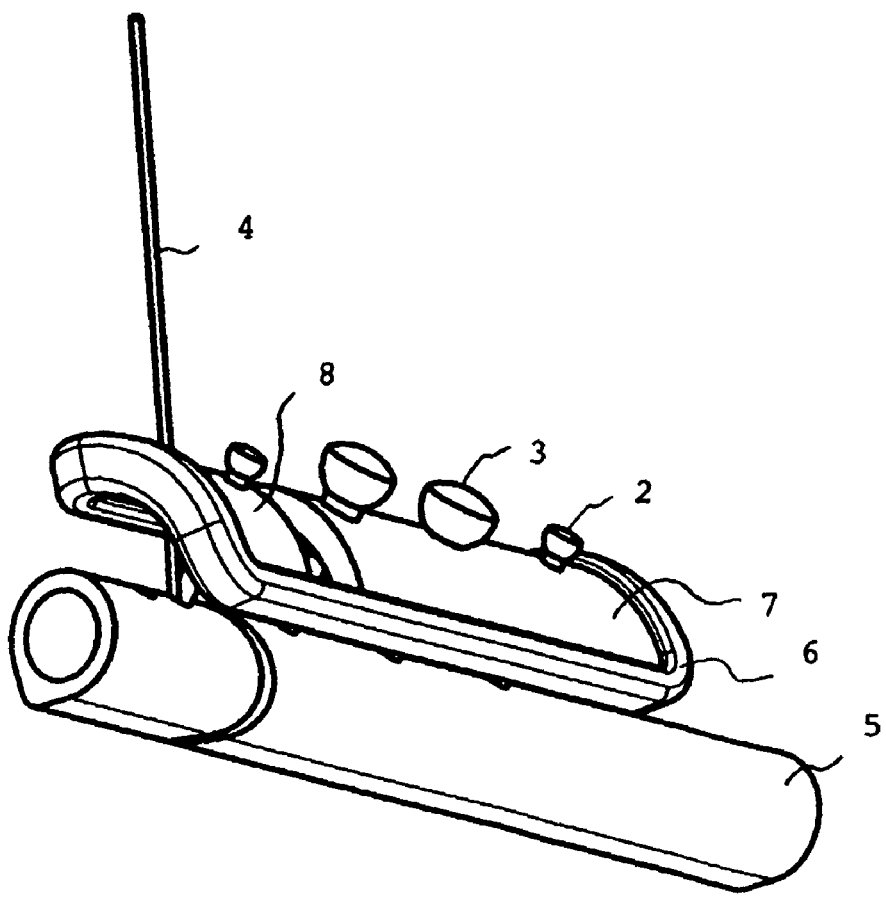
FIG. 4 is a perspective view of a third embodiment of the present invention.

FIGS. 3 and 4 show two examples of embodiments in which the chassis 1, 7, 8 is placed in a bracing 6. The function of the bracing 6, preferably made of steel, is to increases the bending rigidity.

Figure 2:
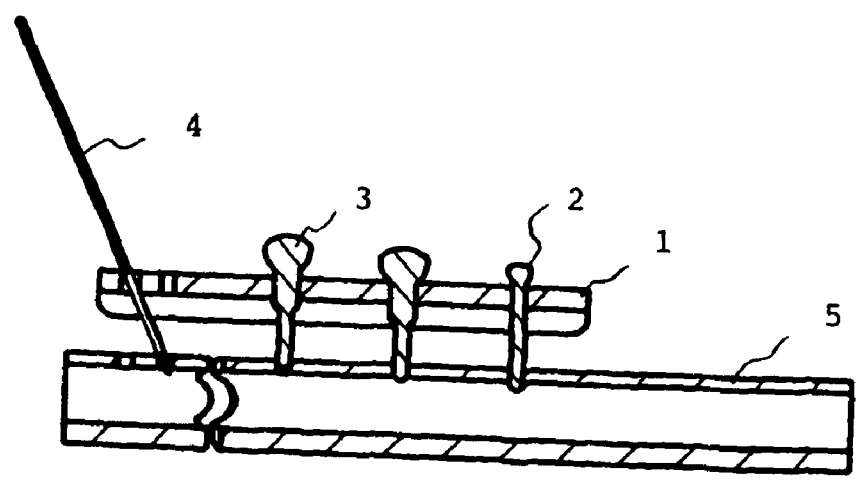
FIG. 2 is a cross sectional view of the system of FIG. 1.

The only difference between the embodiments of FIGS. 1, 2 and 3 is the bracing.

In the embodiment of FIG. 4 the chassis 1 has been divided into two chassis parts 7, 8. A gap is formed between the chassis part 7, 8 and the chassis parts 7, 8 may move in an axial direction towards and away from each other. The purpose of the two chassis parts 7, 8 is that in some cases there may be a desire for a compression or distraction force at the fracture. In which case the chassis part 7, 8 are to be moved towards or away from each other after fixation to the fractured bone structure 5. In all other aspects this embodiment corresponds to the other embodiments.

Even though the present invention is described in connection with external fixation a person skilled in the art realises that it may also be used for internal fixation.

The invention claimed is:

1. A system for fixation of fractures comprising a polyethylene chassis and one or more one-piece fixation elements in the form of screws and/or pins which are adapted to be received in a bone structure, wherein each fixation element is also received in the polyethylene chassis and wherein the polyethylene chassis is made of UHMWPE (ultra high molecular weight polyethylene) which has an elasticity giving a locking effect by friction on the fixation elements in such a way that said fixation elements are frictionally engaged by said UHMWPE chassis as said fixation elements are received by said UHMWPE chassis and thereby are capable of being locked by friction regarding movement in axial, rotational and angular directions as said fixation elements are received by said UHMWPE chassis, said UHMWPE chassis being spaced from said bone structure when said fixation elements are frictionally engaged by said chassis.

2. The system of claim 1, wherein the screws of the fixation elements are screwed into the chassis and bone structure in such a way that the screws move equidistantly in the chassis and the bone structure.

3. The system of claim 2, wherein the system is fixed in a force neutral form.

4. The system of claim 3, wherein no axial forces are transferred to the screws or pins after fixation.

5. The system of claim 1, wherein the chassis is received in a rigid bracing.

6. The system of claim 5, wherein the bracing is made of steel.

7. The system of claim 5, wherein the chassis is made of two parts received displaceable in an axial direction in relation to each other in the bracing and that a gap is formed between the two chassis parts.

8. The system of claim 1, wherein the chassis is placed at a distance from and not in contact with the underlying bone structure or skin.

9. The system of claim 1, wherein the chassis is fixed to both sides of a fractured area whereby a bridge span is formed between bone fragments of the bone structure.

10. The system of claim 1, wherein each fixation element comprises a pin having a first diameter, said UHMWPE chassis having a hole for receiving each pin, each of said holes having a second diameter that is smaller than the first diameter such that the fixation elements are frictionally engaged by said UHMWPE chassis as said fixation elements are received by said UHMWPE chassis.

11. The system of claim 1, wherein each fixation element comprises a screw, said UHMWPE chassis having a first condition free of holes and a second condition in which each fixation element extends through a hole in the chassis UHMWPE formed by said fixation element such that said fixation elements are frictionally engaged by said UHMWPE chassis as said fixation elements are received by said UHMWPE chassis.

12. The system of claim 1, wherein each of said fixation elements has a first end that engages said bone structure and a second end that is spaced from said bone structure, said UHMWPE chassis being positioned between said first end and said second end and being spaced from said first end when said fixation elements are frictionally engaged with said UHMWPE chassis.

* * * * *